United States Patent [19]
Levine

[11] Patent Number: 5,423,825
[45] Date of Patent: Jun. 13, 1995

[54] SPINAL FUSION INSTRUMENTS AND METHODS

[76] Inventor: Andrew S. Levine, 9055 Katy Freeway, Suite 450, Houston, Tex. 77024

[21] Appl. No.: 896,304

[22] Filed: Jun. 10, 1992

[51] Int. Cl.$^6$ ............................................. A61B 17/32
[52] U.S. Cl. ........................................ 606/86; 606/83; 606/84; 606/79; 606/172; 606/99; 81/454; 29/275
[58] Field of Search ......................... 606/60, 79, 84, 83, 606/82, 100, 105, 184, 183, 167, 172, 86, 87, 99; 30/167, 169, 344; 81/451, 452, 454, 457, 458; 29/254, 255, 275

[56] References Cited

U.S. PATENT DOCUMENTS

| | | | |
|---|---|---|---|
| 2,292,657 | 8/1942 | Priest | 81/453 |
| 2,519,811 | 1/1948 | Alexander | 81/454 |
| 2,893,455 | 12/1956 | Lindberg | 81/453 |
| 4,210,145 | 7/1980 | Nestor | 606/172 |
| 4,545,374 | 10/1985 | Jacobson | 606/83 |
| 4,586,496 | 5/1986 | Keller | 606/84 |

FOREIGN PATENT DOCUMENTS

| | | | |
|---|---|---|---|
| 1200834 | 12/1959 | France | 145/52 |
| 470903 | 2/1992 | France | 606/79 |
| 923531 | 4/1982 | U.S.S.R. | 606/79 |
| 1202566 | 1/1986 | U.S.S.R. | 606/84 |

*Primary Examiner*—Robert A. Hafer
*Assistant Examiner*—David J. Kenealy
*Attorney, Agent, or Firm*—Conley, Rose & Tayon

[57] ABSTRACT

An instrument for harvesting an iliac bone graft comprises an elongate handle having a proximal gripping portion terminating in a substantially blunt striking surface, and a distal working portion including a pair of longitudinally extending, transversely spaced apart blade retaining slots. A pair of chisel-type blades are adapted for being releasably, lockably housed in the slots. The blades are retained in the slots by set screws, and by overhanging lips which engage the blades when fully inserted in the slots. An instrument for inserting an iliac bone graft into a disc space comprises an elongate handle having a proximal gripping portion terminating in a substantially blunt striking surface, a distal working portion including an enlarged abutment head on its terminal end, and a slide portion disposed between the gripping portion and the working portion, the abutment head having a distal abutment surface for engaging an iliac bone graft. A retainer member is disposed on the slide portion and is slidable between the abutment head and the gripping portions. The retainer member includes a pair of retaining fingers having proximal ends mounted on the retainer member and free distal ends which extend distally beyond the abutment surface of the abutment head when the retaining member is in its distalmost position. The distal ends of the retaining fingers are spring biased toward one another. The abutment head has stop lugs disposed on side extensions for limiting the travel of the abutment head into a disc space.

22 Claims, 7 Drawing Sheets

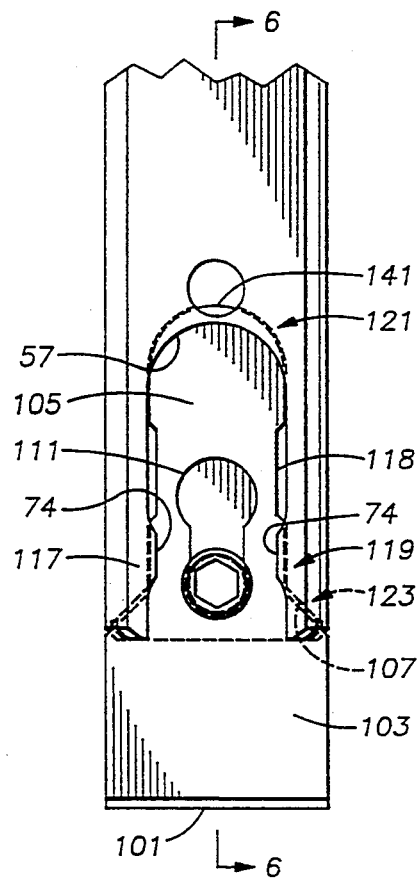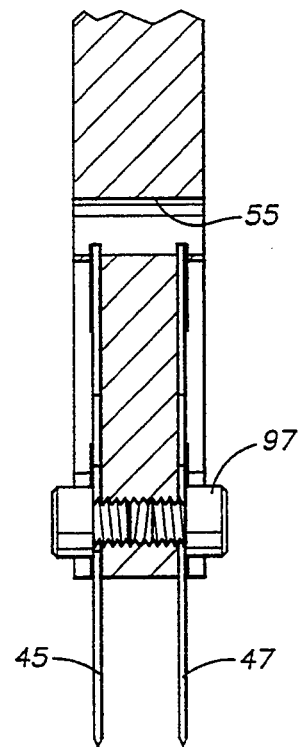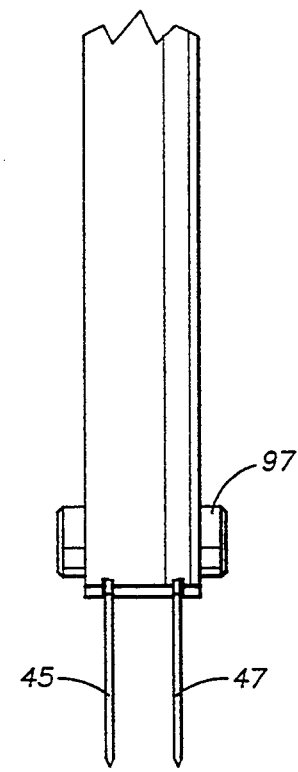
FIG. 5  FIG. 6  FIG. 8
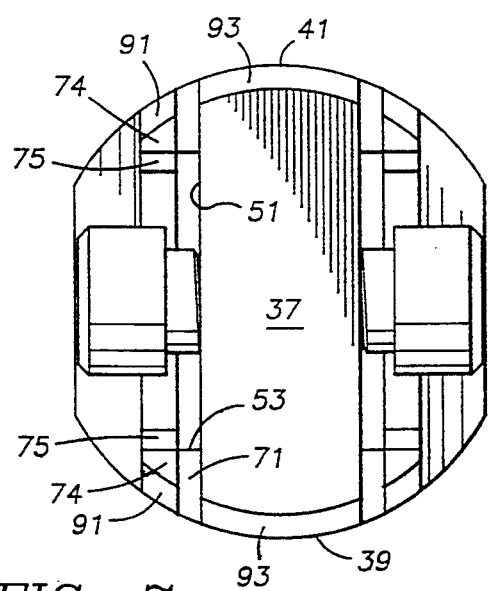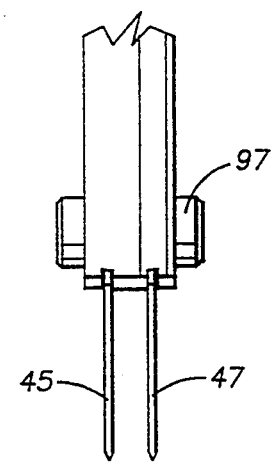
FIG. 7  FIG. 9

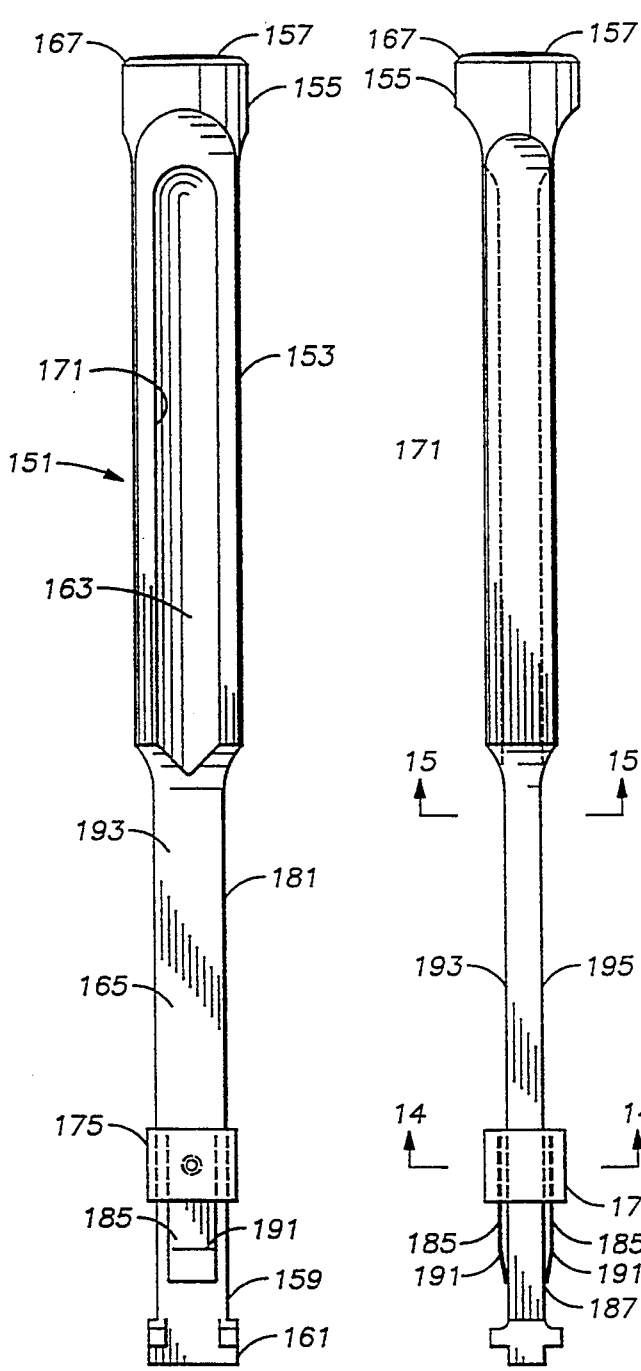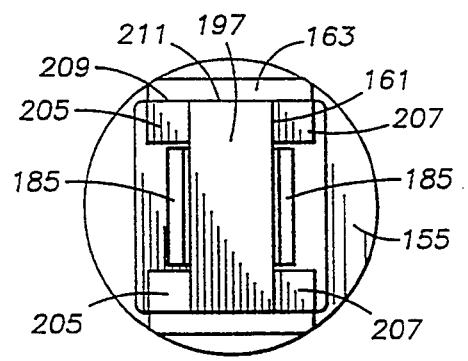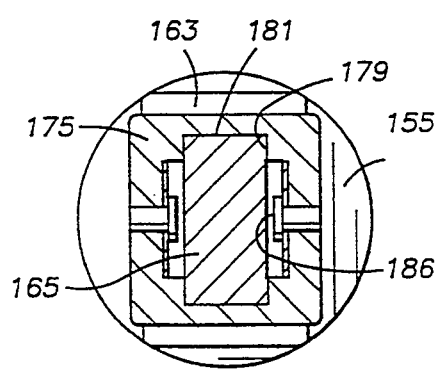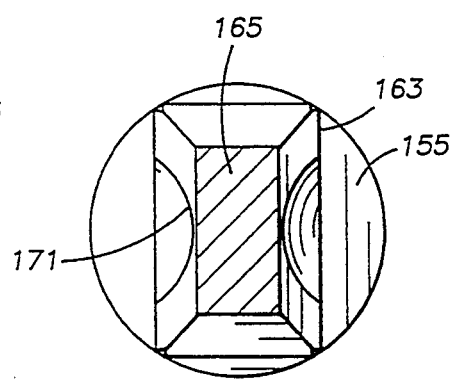
FIG. 11  FIG. 12  FIG. 13  FIG. 14  FIG. 15

SPINAL FUSION INSTRUMENTS AND METHODS

BACKGROUND OF THE INVENTION

The present invention relates to the field of surgical instruments, and more particularly to the field of instruments for use in spinal fusion procedures. More particularly still, the present invention relates to an extraction instrument for use in harvesting an iliac bone graft, and an insertion instrument for use in placing the graft in a spinal disc space. The instruments of the present invention have particular utility in the course of performing anterior cervical fusion procedures according to a modified Robinson technique, but may also be used in other types of procedures, for example, lumbar interbody fusions.

The human spine, vertebral column, or backbone comprises a plurality of stacked vertebrae, each vertebra consisting of a ventral body, or centrum, surmounted by a Y-shaped neural arch. Together the centrum and neural arch surround an opening, the vertebral foramen, through which the spinal cord passes. The centrums are separated by cartilaginous intervertebral discs, which help to cushion shocks to which the vertebral column is subjected. The human spine comprises seven (7) cervical or neck vertebrae, twelve (12) thoracic, five (5) lumbar, and fused sacral and caudal vertebrae.

From time to time, people may suffer from one of various diseases which affect the intervertebral discs. The discs may become inflamed, swollen, or misshapen, they may break down or deteriorate, or they may even "slip" or protrude partially out of their intervertebral housings, or disc spaces. Sometimes such disease processes are precipitated by an injury or the like. When this happens, the affected disc or discs can exert undue pressure on the spinal cord or spinal nerves extending from it, which can cause extreme pain or discomfort, restrict movement, or even disable the unfortunate victim. Sometimes the affected disc or discs cannot be effectively treated or rehabilitated, and in such cases complete removal of the disc(s) is required.

Removal of diseased or otherwise hopelessly impaired discs may be accompanied by fusion of the adjoining vertebrae with a bone graft taken from elsewhere in the body. In a fusion procedure, the bone graft is inserted in the disc space in place of the removed disc, and the vertebrae above and below the graft grow together with, or become "fused" to, the graft. The resulting fused joint is no longer freely flexible, but the pain is eliminated, the patient will still have some movement around the joint, and he can resume most of his normal life's activities.

When the cervical discs are affected, the fusion procedure is typically accomplished from the front, or anterior, of the neck. This procedure is known to those skilled in the art as an anterior cervical fusion, or an anterior interbody cervical fusion. Several different techniques have been developed for effecting an anterior cervical fusion. According to one such technique, a cylindrical or dowel-shaped graft is inserted into a matching cylindrical space which comprises the disc space and an arcuate portion on the upper and lower sides, or the roof and floor, of the disc space. This is known as a Cloward fusion. Specialized instruments have been developed for use in the Cloward procedure, for assisting in the graft harvesting and insertion steps. Such instruments have been designed, of course, to accommodate the harvesting of a round graft and the handling of that round graft in the insertion phase. Due to drawbacks in the Cloward technique, however, it has been diminishing in popularity of late. One major drawback of the Cloward fusion is that the vertebrae which bound the disc space are weakened due to the arcuate portion removed from them. This is undesirable because the weakened vertebrae are more susceptible to additional injury or damage. This weakening of the vertebrae also makes the Cloward procedure undesirable for fusing two adjacent discs, because the middle vertebra of the three affected vertebrae would have an arcuate portion removed from both its upper and lower faces.

Another prior art technique for performing cervical fusions is the Bailey-Badgley procedure. In a Bailey-Badgley fusion, the graft is shaped somewhat like a tall wedge with a rounded nose, and as is the case with the Cloward technique, the matching space comprises not only the disc space, but also some space from the roof and floor of the disc space. In the Bailey-Badgley procedure, the portions removed from the roof and floor of the disc space are not arcuate, but flat. The Bailey-Badgley fusion suffers from the same major drawbacks as the Cloward technique, in that the vertebrae which bound the disc space are weakened due to the portion removed from them. Thus, the Bailey-Badgley procedure is also undesirable for fusing two adjacent discs.

The most popular cervical fusion technique of late is that of Robinson. In the Robinson technique, an iliac bone graft is inserted into the disc space, with little or no removal of surrounding tissue to accommodate the graft, contrary to both the Cloward and Bailey-Badgley fusions referred to above. The Robinson technique thus can be used effectively to fuse two adjacent discs. In the Robinson fusion, the iliac bone graft is harvested from the edge of the ilium so that cortical bone is present on three sides of the graft. The iliac bone graft is sized and shaped according to the size and shape of the intended disc space, and inserted into the disc space with the middle cortical edge to the anterior. That results in the graft having cortical bone on all three exposed sides. In a modified form of the Robinson technique, the middle cortical edge is inserted into the disc space first, that is, in a posterior position. This tends to help the surgeon with the graft insertion step, because the leading cortical edge is relatively stiff and curved or "bullet shaped," which assists in slipping the graft past the surrounding tissue at the entrance to the intended disc space.

Although the Robinson and modified Robinson techniques have enjoyed much success of late, there are several major drawbacks with the instruments commonly used in performing these procedures which detract from this success. In the graft harvesting phase, quite often the surgeon will use a single-bladed instrument somewhat like a chisel to make a pair of incisions in the ilium to bound the graft. The blades of such chisel-like instruments may have a dual-tapered edge. One drawback with the single-bladed instrument is a lack of positive control on the size and shape of the graft. The surgeon may inadvertently make the graft too small or too large, by making the incisions too close together or too far apart. In the former event the graft may be unusable, and in the latter event the graft will require excess tooling or reshaping. In addition, while the surgeon may wish to have a graft with substantially parallel upper and lower faces, he may inadvertently fail to make the pair of cuts parallel to one another. This also requires excess tooling or reshaping.

One alternative to the single-bladed harvesting instrument discussed above is a small power saw with two parallel oscillating blades. Although this device gives more control over the size and shape of the graft than the single-bladed instrument, a drawback of the device is that small particles of bone are thrown off around the harvesting site or into the air, which may contaminate the physical surroundings and/or medical personnel in the vicinity. With the increasing incidence of disastrous afflictions such as AIDS, the undesirability of such contamination is clear.

With regard to the insertion phase of the Robinson or modified Robinson procedures, typically the graft will be held with a clamp, forceps, or some other such device to place it into the entry of the disc space. Then the graft will usually be engaged by a rod or punch, the end of which is tapped by a mallet, which drives the graft into the disc space. This technique is undesirable, however, because the rod or punch can slip off the disc, possibly injuring the patient. Moreover, the surgeon has less than full control over the orientation of the graft as it is driven into the space; the graft can rotate in the space, causing undue complications to the procedure. In addition, at times the graft may be driven too far into the posterior portion of the disc space. If the graft is driven too far into the region of the spinal cord or other nerves, serious injury to the patient could occur.

An instrument known as a dowel holder has been used in the past for placing the graft in the disc space and holding it during the insertion step, as an alternative to the clamps, forceps, and rod or punch referred to above. A dowel holder typically includes a rectangular head with distally extending pointed supports at its corners, and a distally extending threaded screw shaft in its center. This instrument is used particularly in the Robinson procedure. A hole is drilled in the middle of the graft, and the threaded shaft is screwed into the hole. The dowel holder may then be manipulated with the graft screwed to it, to enable the graft to be placed in the entry of the disc space. The end of the dowel holder is then tapped, to drive the graft into place. The pointed corners help keep the graft from rotating while being driven into place. A major drawback with this instrument is that the graft is weakened by drilling the hole in it. The graft may split while being driven into place, which of course seriously complicates the procedure. In addition, there is no positive stop on this instrument which prevents the graft from being driven too far into the disc space, leaving the possibility of causing severe injury to the patient if this were to occur.

SUMMARY OF THE INVENTION

The present invention overcomes the problems and drawbacks discussed above, by providing novel and unique instruments for use in spinal fusion procedures, particularly those known as anterior cervical fusions according to a modified Robinson technique, but also in other types of fusions such as lumbar interbody fusions. The present invention comprises an extraction instrument for use in harvesting an iliac bone graft, and an insertion instrument for use in placing the graft in a spinal disc space.

The extraction instrument of the present invention includes an elongated handle with a blunt striking surface on its proximal end, and a distal working portion including a pair of upper and lower blade retaining slots or channels. The handle preferably comprises a solid, substantially circular cylindrical shaft with stepped, diametrically opposed planar portions or flats on its upper and lower faces. The flats reduce the weight of the instrument and provide a grip surface for the surgeon. The sides of the extraction instrument are substantially circular cylindrical and extend continuously from the proximal end of the instrument through its distal working portion.

The retaining slots or channels are adapted for releasably and securely housing a pair of parallel, spaced apart, dual tapered blades. The blades are relatively flat and substantially razor-sharp, and are spaced apart a distance corresponding to the desired height of the graft to be harvested. A transverse bore extends through the handle near the proximal ends of the slots, and communicates with the slots. Overhanging lips are disposed at the proximal ends of the slots and along the sides near their distal ends, to assist in securing the blades in the slots. The blades are retained in the slots by a set screw which is received in a shaped aperture in the blades. The blades each have a wide main body portion which protrudes from the distal end of the handle, and a narrower shank portion which is received in the corresponding slot and which is positively retained in the handle by the set screw and the overhanging lips. The shaped aperture for receiving the set screw is disposed in the shank portions of the blades.

The blades include recessed areas along the midportion of the shank which must be placed in register with the overhanging side lips to seat the blades fully against the slot floor, or to remove them from the slots. With the blades fully seated, they can be moved proximally to slide them under the three overhanging lips. Tightening the set screws fully secures the blades against substantial movement with respect to the handle. The distal end face of the handle provides a convenient, positive stop for the depth to which the extraction tool is driven.

The extraction tool of the present invention enables the surgeon quickly and easily to obtain grafts which are all of substantially uniform size and shape. This minimizes the reshaping required to make the graft fit the disc space. This also avoids the floating or scattered debris created by the dual-bladed power saw, referred to above.

When the graft has been harvested, it is shaped as necessary, and is also trimmed after measuring with a special gauge so that it will be centered in the disc space from front to back. Then the insertion instrument of the present invention is used to place the graft into the disc space, and drive it surely, safely, and squarely into its final position. The insertion tool of the present invention includes a solid, elongated handle having a blunt striking surface on its proximal end face, and a distal working portion including an enlarged abutment head. The handle includes a gripping portion extending along approximately half the length of the instrument, and a slide or working portion extending between the gripping portion and the abutment head. The slide or working portion of the instrument is generally rectangular.

A bone graft retainer member is slidably disposed on the slide portion of the instrument. The retainer member is substantially rectangular in outer configuration, and includes a generally rectangular bore in which the slide portion is received. The bore includes rectangular-shaped grooves or tracks on two of its opposite faces for receiving the sides of the slide portion therein. The retainer member is free to slide easily along the slide portion between the gripping portion and the abutment head, but is restrained against transverse movement during such sliding travel.

The retainer member includes two relatively flat, spring steel retaining blades or fingers having their proximal ends mounted inside the bore of the retainer member and their distal ends extending distally from the retainer member. The fingers are bent or bowed such that their distal ends are spring biased toward one another. When the retainer member moved distally as far as possible, the tips of the fingers clear the distal end of the abutment head, and flex inwardly toward one another. When the retainer member is moved proximally, the tips are forced to flex outwardly such that they engage the surfaces of the slide portion with some spring tension. This flexing or spring tension allows the fingers to grip the bone graft and permits its manipulation by the instrument in the graft insertion process.

The abutment head has extension portions which include pairs of upper and lower stop lugs which are spaced apart sufficiently to allow the fingers to move between them as the retainer member slides along the slide portion of the handle. The stop lugs are all recessed from the end face of the abutment head a distance which is substantially the desired setback distance of the anterior face of the bone graft from the anterior edge of the intended disc space.

The automatic stop lugs positively prevent over-insertion of the head of the instrument into the disc space. The setback of the lugs, along with use of the special gauge for trimming the graft, result in the substantial centering of the graft in the disc space. Thus, the graft cannot be inserted too far in the space. In addition, due to the positioning of the stop lugs and the square abutment of the graft against the distal face of the abutment head, the graft is substantially prevented from rotating or becoming skewed in the space during insertion.

The extraction and insertion instruments of the present invention thus provide a quick, easy, safe, and sure solution to the problems referred to above in connection with prior art devices and techniques. Use of the instruments of the present invention will shorten the surgical procedures, and thus help to reduce their cost. They will also help to reduce the risk of accidental injury to the patient during these procedures.

The instruments of the present invention are also relatively easy for the skilled surgeon to manipulate. They are also very durable, easy to make in a variety of useful sizes, and readily transportable, for example in the manner of a surgeon's kit. The blades of the extraction tool are easy to remove, and to clean, sharpen, or replace if necessary.

These and other objects and advantages of the invention will become apparent from the following description of the preferred embodiment when read in conjunction with reference to the following drawings, wherein:

BRIEF DESCRIPTION OF THE DRAWINGS

FIG. 5 is a plan view of the distal portion of the extraction instrument shown in FIG. 1, with the blades installed.

FIG. 6 is a part sectional, part side elevational view of the distal portion of the extraction instrument shown in FIG. 5.

FIG. 7 is a distal end view of the extraction instrument of FIG. 1.

FIGS. 8 and 9 are side views of the distal portions of extraction instruments according to the present invention, showing different spacing of the dual tapered blades.

FIG. 11 is a plan view of the insertion instrument of FIG. 10.

FIG. 12 is a side view of the insertion instrument of FIG. 10.

FIG. 13 is a distal end view of the insertion instrument of the present invention shown in FIG. 10.

FIG. 14 is a sectional view of the insertion instrument of FIGS. 10-12, taken along lines 14—14 shown in FIG. 12.

FIG. 15 is a sectional view of the insertion instrument of FIGS. 10-12, taken along lines 15—15 shown in FIG. 12.

DESCRIPTION OF THE PREFERRED EMBODIMENTS

Figure 1:
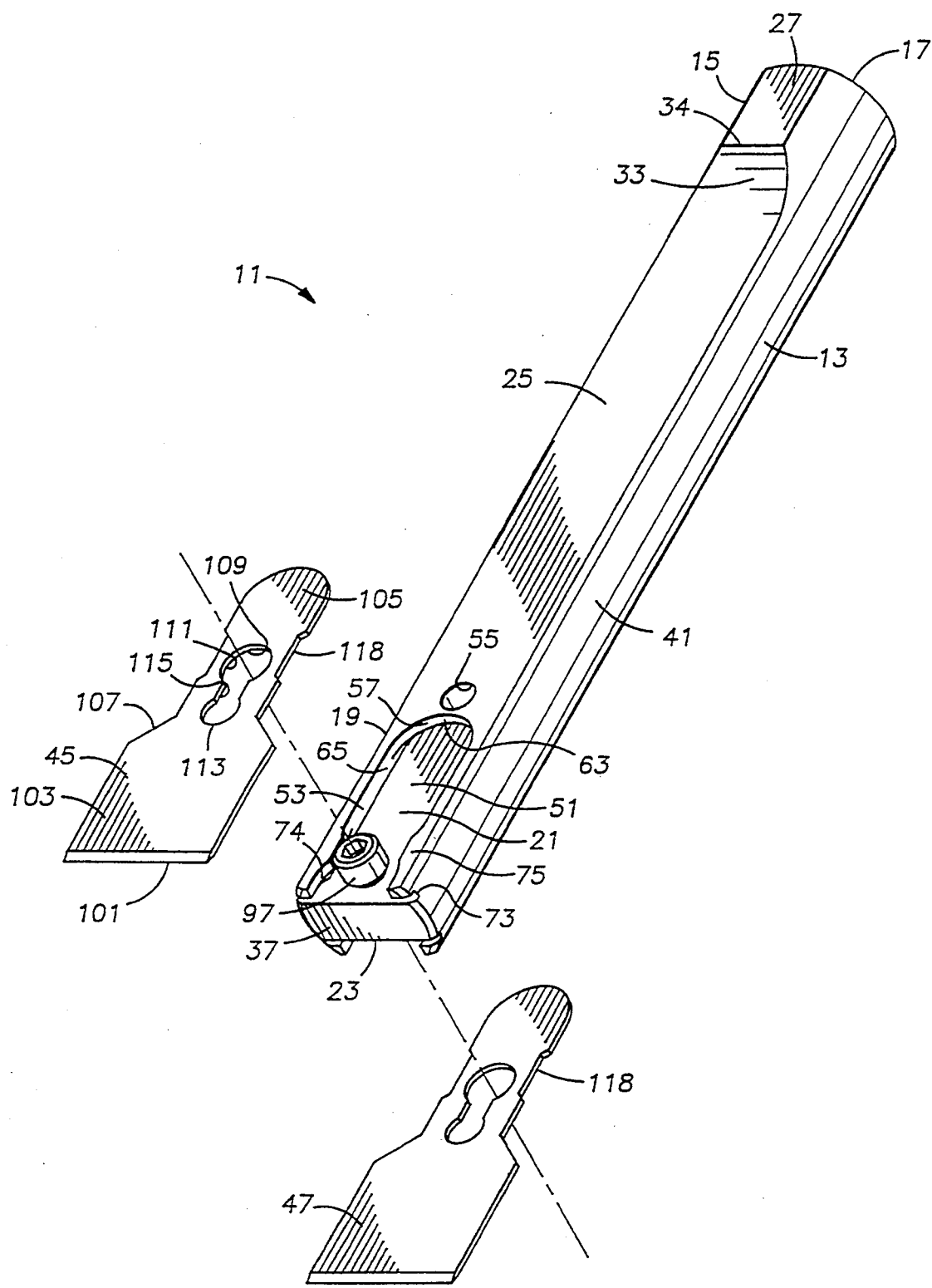
FIG. 1 is an exploded pictorial view of the extraction instrument of the preferred embodiment of the present invention.
Figure 2:
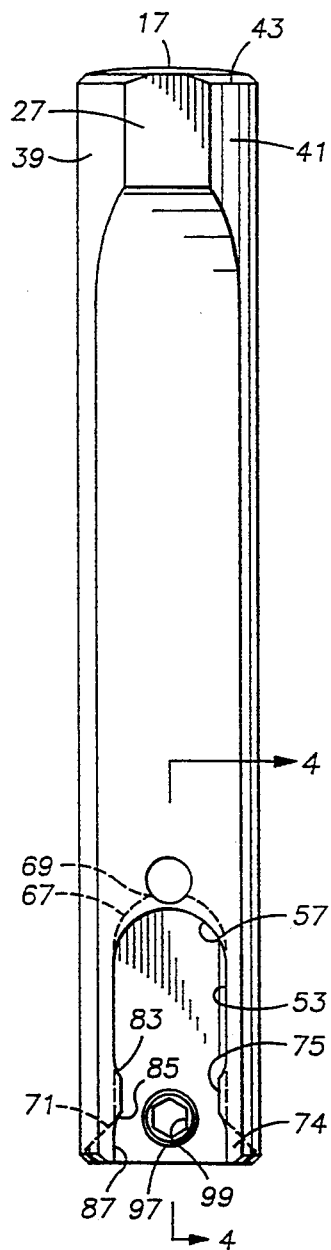
FIG. 2 is a plan view of the instrument of FIG. 1, without the blades.
Figure 3:
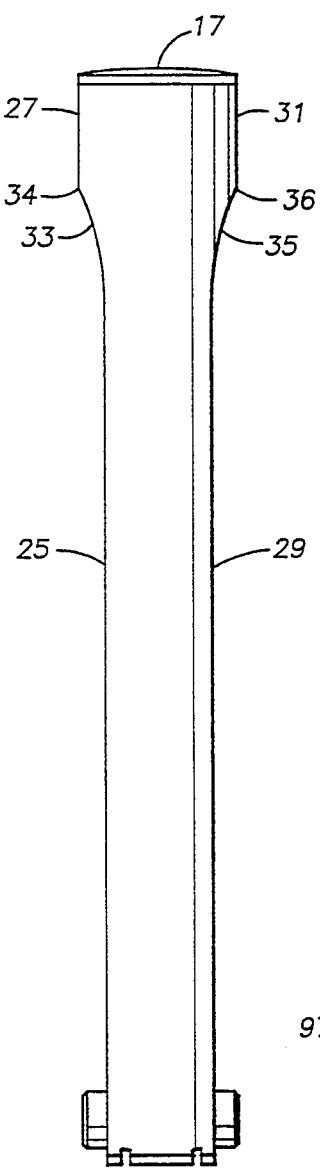
FIG. 3 is a side view of the instrument of FIG. 1, again without the blades.
Figure 4:
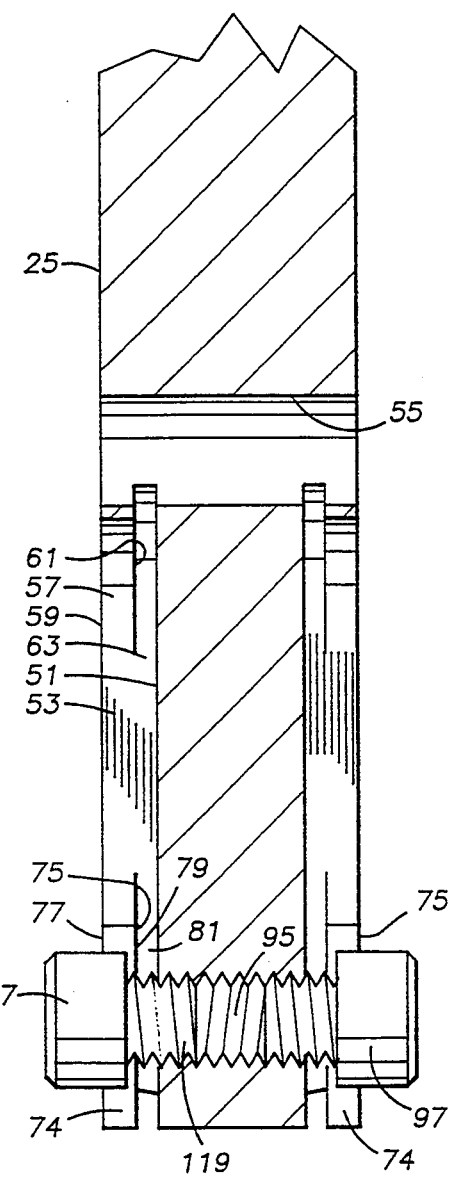
FIG. 4 is an enlarged, fragmentary sectional view of the instrument of FIG. 2, taken along the lines 4—4 of FIG. 2.

Referring initially to FIGS. 1-9, and particularly to FIG. 1, there is shown an extraction instrument according to the present invention, indicated generally at 11, for use in removing an iliac bone graft from the pelvis of a patient for subsequent use in an anterior cervical fusion procedure for that patient, as discussed above. For clarity and ease of reference, in the following discussion of the instrument shown in FIG. 1 it will be assumed that it is oriented as shown in that figure, with the "upper" side or face of the instrument being toward the upper edge of the page and the "lower" side or face toward the lower edge. It should be understood, however, that in use, the instrument 11 is simply manipulated and oriented by the surgeon in whatever manner or direction is necessary to accomplish its purpose; in that sense, there is no single upper or lower side or face of the instrument.

The extraction instrument 11 includes an elongated handle 13 having a proximal portion 15 terminating in a substantially flat or blunt striking surface 17 on its end face, and a distal working portion 19 including a pair of upper and lower blade retaining slots or channels 21, 23, respectively. Handle 13 is preferably configured in the form of a solid, substantially circular cylindrical shaft with stepped, diametrically opposed planar portions or flats 25, 27 and 29, 31 (see FIG. 3) on its upper and lower faces, respectively. Flats 25, 27 and 29, 31 are all substantially parallel to one another. A smooth, arcuate or concave surface 33 on the upper side of instrument 11 serves as a transition surface between flats 25 and 27, and a correlatively shaped smooth, arcuate or concave surface 35 on the lower side of the instrument serves as a transition surface between flats 29 and 31. Flats 27, 31 intersect transition surfaces 33, 35 at edges 34, 36, respectively, and extend from those edges to the proximal end of the instrument 11.

Flats 27, 31 are farther from the central longitudinal axis of the instrument 11 than are flats 25, 29. Thus, the handle 13 is thinner along its midportion than it is at its proximal end portion 15, and remains at substantially that same reduced thickness through the distal working end portion 19 to terminal end 37. The flats 25, 29 serve both to reduce the weight of the instrument and to provide a grip surface for the surgeon to grasp securely between his or her fingers and thumb during the graft harvesting procedure.

The sides 39, 41 of extraction instrument 11 are substantially circular cylindrical in configuration and extend in a smooth, continuous fashion from the proximal end of the instrument through its distal working portion. The proximal edges of the arcuate sides 39, 41 and the proximal edges of the flats 27, 31 are slightly rounded, as shown at 43, between such edges and the striking surface 17 to eliminate any sharpness and facilitate safe handling of the instrument by the surgeon or other personnel.

Referring now particularly to FIGS. 2 through 7 along with FIG. 1, upper and lower retaining slots or channels 21, 23 of distal working portion 19 of extraction instrument 11 are adapted for releasably and securely housing a pair of dual tapered, chisel-type blades 45, 47. Upper blade 45 is housed in upper slot 21, and lower blade 47 is housed in lower slot 23. Upper slot 21 is substantially identical to lower slot 23, and upper blade 45 is substantially identical to lower blade 47, so only one set of blades and slots will be described in further detail. It should be understood, however, that the description of one such set of blades and slots will also apply to the other.

Slot or channel 21 includes a planar base surface 51 and side walls 53 which are substantially perpendicular to base 51. Base surface 51 is substantially parallel to flat surface 25, and recessed from such surface toward the central longitudinal axis of the instrument 11 by an amount equal to the height of side walls 53. Planar base surface 51 of slot 21 extends from the distal terminal end 37 of instrument 11 to and intersecting with a transverse bore 55, such that the slot is in communication with the bore. Bore 55 extends through the instrument from upper flat surface 25 through lower flat surface 29, and is substantially perpendicular to such surfaces. At the proximal end portion of the slot 21, there is disposed a flat overhanging lip 57 comprising an upper surface 59 which is continuous with the flat surface 25, and a lower surface 61 which is parallel to upper surface 59 and spaced therefrom a distance less than the height of side walls 53, thus leaving a clearance space 63 between the lower surface 61 of lip 57 and the base surface 51 of slot 21. The exposed edge of lip 57 is substantially circular in configuration and joins walls 53 on both sides of the instrument part way along the axial length of slot 21, as shown at 65, such that a smooth transition is formed between lip 57 and walls 53.

Side walls 53 are parallel to one another along a major portion of slot 21, but near the proximal end of the slot, and near the transition area 65 between lip 57 and walls 53, they begin to curve toward one another in substantially circular fashion in a proximal direction, as shown at 67, until they intersect with transverse bore 55, as shown at 69. Near the distal portion of the slot 21, walls 53 fan outwardly, that is, toward sides 39, 41 of instrument 11, in a distal direction as shown at 71 until they intersect with sides 39, 41 adjacent the distal end of the instrument, as shown at 73.

On each side of the slot 21 near its distal end, there is disposed a flat overhanging lip 74 having an inwardly extending lobe 75 on its proximal end. Each lip 74 comprises an upper surface 77 which, like the upper surface 59 of lip 57, is continuous with flat surface 25, and a lower surface 79 which is parallel to upper surface 77 and spaced therefrom a distance less than the height of side walls 53, thus leaving a clearance space 81 between the lower surfaces 79 of lips 74 and the base surface 51 of slot 21. Clearance space 81 is substantially the same in height from base surface 51 as clearance space 63.

Beginning at an inwardly tapering surface 83, lobes 75 of lips 74 extend inwardly toward one another, resulting in a reduced width tier slot 21 at the location of the lobes. The lobe surfaces fan outwardly from the distal ends of the lobes as shown at 85, until the side walls 87 of the lips 74 are spaced apart a distance substantially the same as the walls 53 in the midportion of the slot 21.

The distal ends of the lips 74, and the edges of the handle 13 between the distal terminal end 37 of the instrument 11 and the sides 39, 41, are beveled as shown at 91, 93, respectively, to eliminate any sharpness, which facilitates insertion of the instrument into its working position adjacent the patient's pelvis during the graft harvesting procedure, and to reduce the risk of accidental injury to the patient during use of the instrument by the surgeon.

A threaded, transversely extending bore 95 is disposed through the instrument 11 between base surfaces 51 of the upper and lower slots 21, 23, for receiving a pair of set screws 97 therein. Set screws 97 may include a shaped receptacle 99, such as one having a hexagon shape, for receiving a correlatively shaped wrench or other actuator for securely tightening or loosening the set screws.

Instrument 11 further includes blades 45, 47 which are shaped to be received and securely retained in the slots 21, 23. As indicated above, blades 45, 47 are substantially identical, so only one, that is, blade 45, will be described further in detail. The description of blade 45 applies to blade 47, as well. Blade 45 is a relatively flat member having a dual tapered, substantially razor-sharp edge 101. By "dual tapered" we mean that the distal end of the blade 45 tapers on both its upper and lower faces toward and creating sharp edge 101. It is preferred that blade 45 taper substantially equally on both faces to form sharp edge 101. The blade 45 has a relatively wide main body portion 103, and a narrower shank portion 105 located proximally of the main body portion 103. A tapered surface 107 extends between the main body portion 103 and the shank portion 105 on both sides of the blade. An aperture 109 is centrally disposed in the shank portion of the blade, and includes a relatively large circular portion 111 at its proximal extremity, a smaller circular portion 113 at its distal extremity, and a straight portion 115 between the two circular portions 111, 113. The straight portion 115 is narrower in width than the diameters of both circular portions 111, 113. The larger circular portion 111 has a diameter slightly larger than the diameter of the head of set screw 97, and the smaller circular portion 113 has a diameter smaller than the head of the set screw, but larger than the diameter of the threaded portion 119 of the set screw. The straight portion 115 has a width greater than the diameter of threaded portion 119.

In order to secure the blade 45 to the instrument 11, the circular portion 111 of the blade can be placed over the set screw 97 with the shank 105 facing the proximal end of the slot 21, and the lower face of blade 45 flush with surface 51. Then, blade 45 can be moved axially in a proximal direction, so that the shank 119 of set screw 97 traverses the straight portion 115 of the aperture 109 and comes to rest in the smaller circular portion 113. The set screw is then tightened, for example using an Allen wrench or other such actuator, which tightens the blade against the surface 51. Since the head of the set screw is larger in diameter than the circular portion 113 of the aperture, the set screw prevents the blade from being removed from the instrument in a direction transverse to the instrument. In addition, the thickness and sizing of the blade are such that it tits under the lips 57, 74 in the clearance spaces 63, 81 between the lips and the surface 51 when fully proximally inserted in the slot 21, so that the blade is also retained in the instrument 11 by the overhanging lips. The blade 45 includes recessed areas 118 along the midportion of the shank 105 which are in register with the lips 74 when aperture 111 is placed over set screw head 97, thus permitting the blade to become seated against the surface 51, prior to fully sliding the blade in a proximal direction to lock it in place under the overhanging lips. The fully inserted position of the blade 45 in the slot 21 is shown in FIG. 5, where lips 74 are shown as extending over the side edges of the shank portion 105 of the blade at 117, 119, and lip 57 is shown as extending over the proximal end of the shank portion 105 at 121. In addition, the tapered surfaces 107 between the main body 103 and the shank 105 of blade 45 may be supported by the flared surfaces 71 of the walls 53 of slot 21 as shown at 123, which provides further support for the blade 45.

When the blade 45 is fully seated in the slot 21 and set screw 97 is securely tightened against it, the blade is firmly, securely retained in the instrument 11 against substantial movement with respect to the handle. This applies equally to the lower blade 47 when it is secured in its respective slot 23. When both blades are thus secured in the instrument 11, it is ready for use in the graft harvesting procedure.

Figure 16:
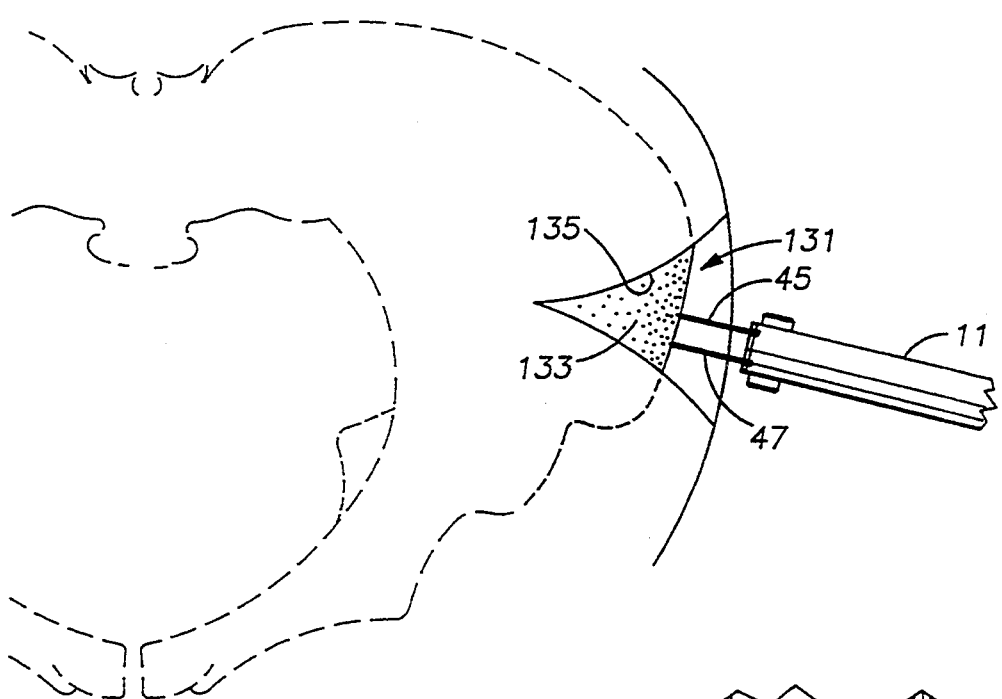
FIG. 16 is a pictorial, schematic representation of the extraction instrument of the present invention just prior to being driven into the iliac crest of a patient.
Figure 17:
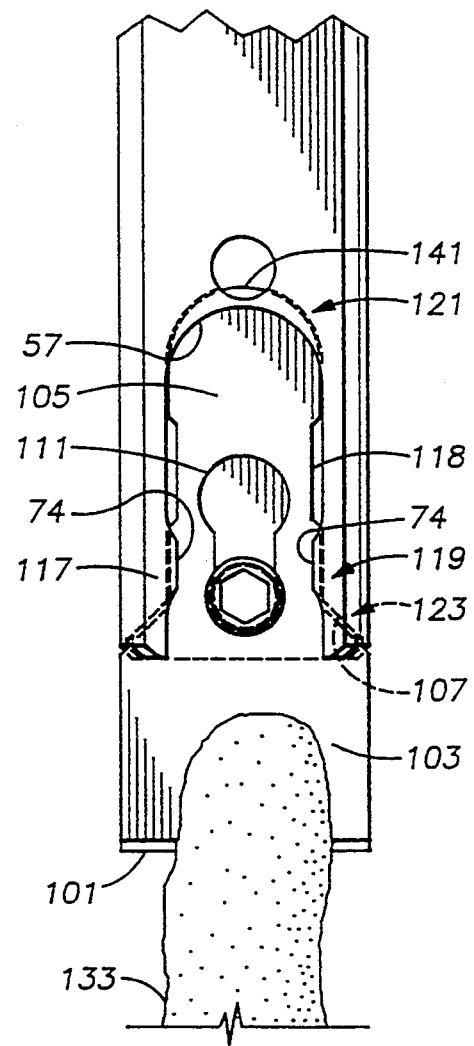
FIG. 17 is a view similar to FIG. 5, but also including a representation of the extraction instrument of the present invention after being driven into the iliac crest of a patient.

As illustrated schematically in FIGS. 16 and 17, when the selected portion 131 of the ilium 133 of the patient is surgically exposed (as indicated, again schematically, by making an incision 135 in the covering tissue at the selected bone graft removal site 131), the surgeon places the instrument 11 against the pelvis with the edges 101 of the blades 45, 47 against the surface of the bone. As indicated above, normally the graft is taken from an outer edge of the ilium, that is, from the iliac crest, as shown in these Figures so that it will comprise cortical tissue on three of its four exposed sides when inserted into the intended disc space. The longitudinal axis of the instrument is preferably oriented such that it is substantially parallel to the desired direction of penetration of the blades into the ilium. The striking surface 17 of the instrument 11 is then tapped lightly, but firmly, with a small mallet or hammer or the like, so that the blades are driven through the layer of cortical bone into the cancellous bone underneath it, to the appropriate depth. The blades 45, 47 may be sized such that the axial length of their main bodies 103 is the same as the desired depth of penetration, so that when the terminal distal end 37 of the handle engages the surface of the ilium, the desired depth has been reached. It will be appreciated that sizing the blades 45, 47 in this way provides a convenient automatic stop or check on the blade penetration depth, and thus on the size of the graft to be harvested. Penetration of the blades 45, 47 to the full extent of their main bodies 103 is indicated schmetically in FIG. 17.

When the blades 45, 47 of instrument 11 have been driven to the desired depth, the instrument may be rocked gently back and forth, or in various directions as necessary or desired, while in place, until the bone graft is broken away from the remainder of the ilium and may be removed. If necessary or desired, a small chisel or other similar tool or instrument may be employed to assist in the graft removal operation. In that event, the chisel or other instrument may be used to weaken, break or cut away the bone disposed between the blades which is still connected to the remainder of the ilium. This facilitates removal of the graft from the surrounding bone.

With use of the present invention, the grafts when removed will all be of substantially uniform size and shape, with opposed cancellous bone surfaces which are substantially flat and parallel to one another, as are the blades 45, 47. These opposed cancellous bone surfaces will become the upper and lower surfaces of the graft when inserted in the intended disc space. The grafts will all be substantially uniform in size and shape because the blades have a fixed separation distance, they are relatively stiff, and they are held securely in the instrument 11 as described above during the harvesting process. This eliminates the guesswork and the trial and error efforts required by prior art techniques in obtaining properly sized and shaped bone grafts.

Figures 10, 22:
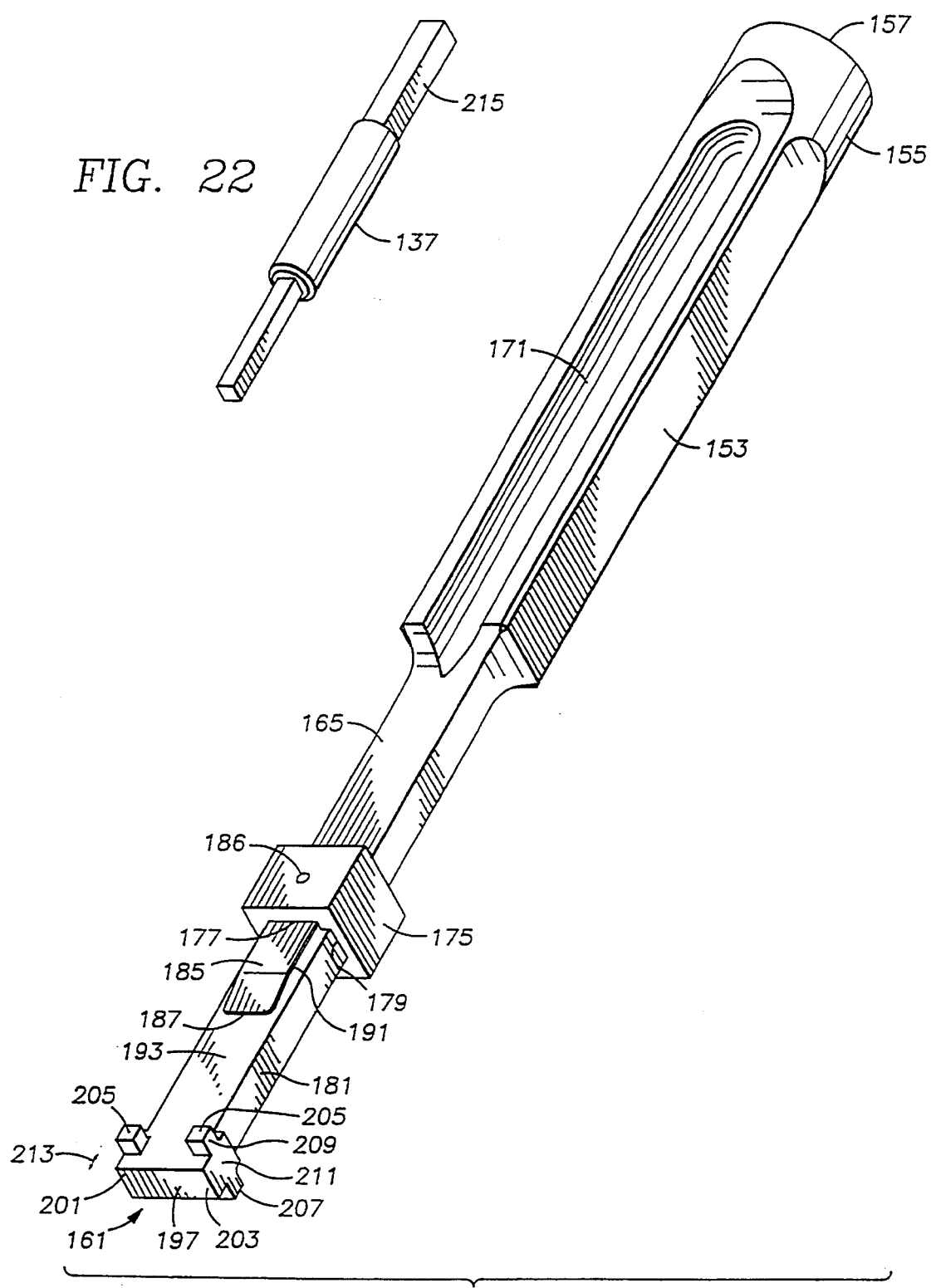
FIG. 10 is a pictorial view of the insertion instrument of the preferred embodiment of the present invention.
FIG. 22 is a pictorial view of a gauge according to the present invention used for aiding the trimming of the iliac bone graft in an amount which permits the graft to be substantially centered in the disc space.

After the graft is separated from the remainder of the ilium as described above, it is removed from the patient's body and shaped as necessary by the surgeon with appropriate instruments such that it will fit properly in the intended disc space. Because with use of the present invention the bone grafts are substantially uniform, typically there will not be as much reshaping as required by the prior art "hit-or-miss" techniques. As is described further below, the graft is also trimmed with the help of a gauge 137 (FIG. 22) so that it will be centered in the disc space from front to back, that is, from anterior to posterior, with substantially the same distance from the anterior part of the graft to the anterior part of the disc space as from the posterior part of the graft to the posterior part of the disc space.

The instruments 11 will preferably be made in different sizes, with different spacing between the blades 45, 47 to accommodate disc spaces of varying heights for patients of varying physical stature. For example, a surgeon's kit may have several different instruments 11, such as three, four, or five instruments, with distances between blades of, for example, from 5 mm to 10 mm, in increments of 1 mm or the like. Use of such various sized instruments 11 is illustrated, for example, in FIGS.

6, 8, and 9, where the spacing between blades is shown to be reduced. Although the distance between the blades may be made smaller to accommodate smaller disc spaces, the remainder of the instrument 11, including the handle 13, should remain the same size since it is adapted to fit easily in the surgeon's hand. Too small a handle, for example, would be difficult for the surgeon to grasp and manipulate.

Following use of the instrument 11, the blades 45, 47 can be removed and cleaned, sharpened, or replaced, as desired. This requires loosening of the set screws 97, sliding the blades distally until apertures 111 coincide with the set screw heads, and lifting the blades from the slots 21, 23. The proximal ends of the blades will clear the lip 57, and the recesses 118 in the shanks 105 of the blades will register with the lips 74, thus permitting removal of the blades from the slots in a perpendicular direction.

If the blades were to become temporarily stuck, rather than risk sustaining an injury from the sharp edges 101 by pulling hard on the blades, removal is facilitated by having the proximal terminal ends 141 of the blades 45, 47 extend slightly into the bore 55, as shown in FIG. 5. Then, a lever can be inserted in the bore 55 to gently pry the blades in a distal direction to free them.

Following removal of the blades from the slots 21, 23, the instrument 11 can then be cleaned and sterilized in preparation for the next graft harvesting procedure. The bore 55 assists in the cleaning operation by providing access to the slots 21, 23, because the bore communicates with the slots. Thus, cleaning fluid or the like can be introduced into the instrument 11 from behind the slots 21, 23, as well as from the front.

Once the bone graft has been removed from the patient's body and shaped to fit in the disc space, the insertion instrument of the present invention is used quickly, surely, and easily to insert the graft into the disc space. The insertion tool of the present invention is shown in FIGS. 10–15, and its use is illustrated in FIGS. 18–21. As shown in these Figures, and particularly in FIG. 10, the insertion tool of the present invention, indicated generally at 151, includes a solid, elongated handle 153 having a proximal portion 155 terminating in a substantially flat or blunt striking surface 157 on its end face, and a distal working portion 159 including an enlarged abutment head 161 on the distal end of the instrument. Handle 153 includes a shaped or profiled proximal gripping portion 163 extending along approximately half the length of the instrument 151 from just below its proximal end, and a slide or working portion 165 below the gripping portion 163, extending from such gripping portion to the enlarged abutment head 161 at the distal end of the instrument. The proximal end portion between the striking surface 157 and the area where the gripping portion begins may have any desired shape, such as circular cylindrical as shown in the Figures, or square, rectangular, or the like. The circular edge around the proximal end of the instrument may be beveled, as shown at 167, to eliminate any sharpness and minimize the risk of accidental injury from use of the instrument. The gripping portion 163 may have a plurality of longitudinally extending grooves 171 therein, a pair of such grooves 171 being shown in the Figures as disposed on opposite sides of the handle 153. Gripping portion 163 is substantially rectangular in shape, but for the pair of grooves 171 disposed in two of its opposite faces. The slide or working portion of the instrument is also generally rectangular in shape. However, in order to minimize the size of the part of the instrument which is introduced into the patient's cervical area, the width and height of the slide or working portion 165 are smaller than the width and height of the gripping portion 163 of the instrument; thus, the slide or working portion is thinner in both side-to-side (see FIG. 11) and front-to-back (see FIG. 12) directions.

A bone graft retainer member 175 is slidably disposed on the slide portion 165 of the instrument 151. Retainer member 175 has a main body which is substantially rectangular in outer configuration, and includes a generally rectangular bore 177 in which the slide portion 165 is received. Bore 177 includes rectangular-shaped grooves or tracks 179 on two of its opposite faces for receiving the sides 181 of the slide portion 165 therein. There is a relatively close, but free, sliding fit between the tracks 179 and the sides 181, so that while the retainer member 175 is free to slide easily along the slide portion 165, it will not move up or down or from side to side to any great extent during such sliding travel. The bore 177 is smaller than the abutment head 161, and also smaller than the gripping portion 163 of the handle 153, so the retainer member 175 can slide only between the gripping portion and the abutment head. In order to assemble the retainer member 175 on the slide portion 165, the retainer member may be formed of two substantially "C" shaped halves which are disposed on opposite sides of the slide portion, with the legs of the "C"s facing one another. The two halves of the retainer member may then be joined, as by spot welding or some other suitable bonding technique, to form a unitary assembly around the slide portion 165.

Retainer member 175 includes two relatively flat, spring steel retaining blades or fingers 185 having their proximal ends mounted inside the bore 177 and their distal ends 187 extending distally from the retainer member. Fingers 185 may be mounted to the opposite sides of the bore 177, adjacent to the sides which include the tracks 179. Small screws, rivets, or pins 186 or the like may be used to secure the fingers 185 inside the bore 177. Alternatively, the fingers may be spot welded or otherwise bonded to the sides of the bore 177. There is a spacing between the surfaces 193, 195 of the slide portion 165 and the opposed sides of the bore 177 to accommodate the fingers and mounting means, without interfering with free sliding movement of the retainer 175 along the slide 165. Fingers 185 are preferably secured one each to the two halves of the retainer member 175 prior to assembly of the halves around the slide portion 165.

Fingers 185 are bent or bowed, as shown at 191, such that their distal ends 187 are spring biased toward one another. The fingers 185 are smaller in width than the tipper and lower surfaces (again, relatively speaking, and as those terms would be understood by reference to FIG. 10) 193, 195 of the slide portion 165, and are substantially centered with respect thereto. When the retainer member 175 is moved distally as far as possible, the tips 187 of the fingers 185 clear the distal end 197 of abutment head 161 of the instrument, and flex inwardly toward one another such that they are closer together than the height of sides 181 of slide portion 165. When the retainer member is moved proximally, for example to the position shown in FIG. 10, the tips 187 are forced to flex outwardly, such that they engage the surfaces 193, 195 with some spring tension. This flexing or spring tension allows the fingers 185 to grip the bone graft and permits its manipulation by the instrument 151 in the graft insertion process, without undue risk of dropping the graft or having it become skewed in the instrument during the insertion procedure.

The abutment head 161 has a height (again, with reference to FIG. 10) which is the same as the height of sides 181 of slide portion 165, and a width which is greater than the width of upper and lower surfaces 193, 195. On the extension portions 201, 203 of the abutment head, which are the portions on the opposite ends of the head which extend beyond sides 181 of slide portion 165, there are disposed a pair of upper stop lugs 205 and a pair of lower stop lugs 207. The stop lugs are substantially rectangular in shape, and are disposed such that their outer faces 209 are flush with the outer end faces 211 of the extension portions 201, 203 of the abutment head. The lugs are spaced apart sufficiently to allow the fingers 185 to move between them as the retainer member 175 slides along member 165. In addition, the stop lugs are all recessed from the flat end face 197 of the head 161, a distance 213 which is substantially the desired setback distance of the anterior face of the bone graft from the anterior edge of the intended disc space. This distance 213 is also substantially the desired spacing or distance of the posterior face of the bone graft from the posterior surface of the intended disc space. With the distance 213 on both the anterior and posterior sides of the graft when it is in place in the intended disc space, it will be appreciated that the graft will be substantially centered in the disc space from front to back, that is, anteriorly-to-posteriorly.

In order to determine the proper sizing of the graft to result in this centered relationship of graft to disc space, the surgeon measures the depth of the disc space, which means the anterior-to-posterior distance, and also the height of the disc space, which means the distance between the vertebra which bound the space. He then scores the graft which has been removed from the ilium as discussed above, to coincide with the measurements thus determined, and to serve as the guides for trimming the graft. Prior to such trimming, however, and in accordance with the present invention, the surgeon will score the graft for depth to remove an additional amount of bone from the graft. This additional amount to be removed from the depth of the graft is determined by placing the desired end of a gauge 137 (FIG. 22) adjacent and parallel to the edge of the graft opposite to the central of the three cortical edges resulting from the harvesting process, described above. The gauge 137 has square ends 215 whose thickness is substantially twice the desired spacing 213; the gauge may have two such ends with different thicknesses to accommodate either of two desired setback distances 213. It will also be appreciated that a surgeon's kit may have several such gauges 137, each with different sized ends. With the end 215 as a guide, the graft is scored for removal of an additional amount of bone from the depth of the graft. With the graft thus scored, it is then trimmed and readied for the insertion operation.

Figure 18:
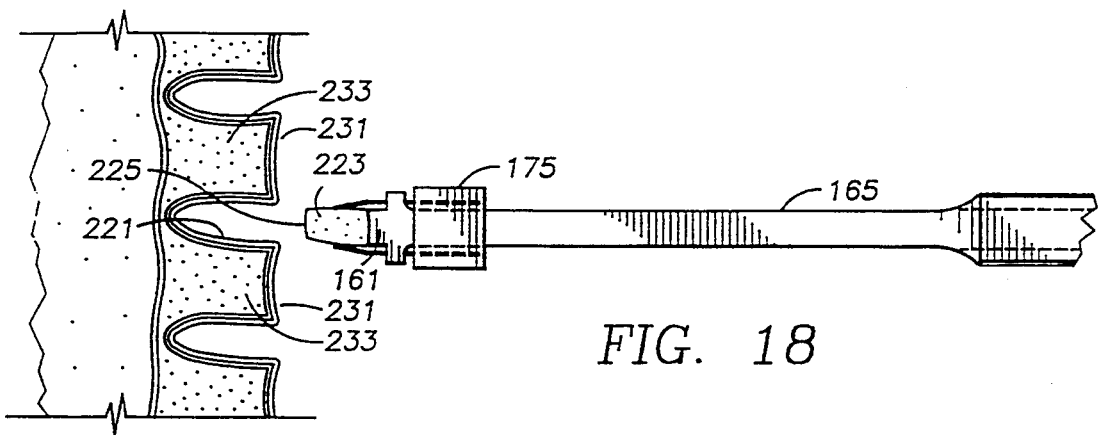
FIGS. 18-21 are schematic representations of the insertion instrument of the present invention being used to insert an iliac bone graft into place in a disc space.

Assuming the graft is properly trimmed, now with reference to FIGS. 18–21, the graft insertion process is illustrated, and is substantially as follows. As shown in FIG. 18, the instrument 151 is poised near the intended disc space 221 such that it is substantially parallel to the direction of desired insertion. The retainer member 175 is in its distal-most position with respect to the slide portion 165, and the graft 223 is held between the fingers 185. The graft is preferably held such that its central cortical edge 225 enters the disc space first, just the opposite from the original Robinson technique, and the remaining two cortical edges are disposed to the sides of the disc space. The surface of the graft 223 which faces the terminal end face 197 of abutment head 161 is substantially flat and engages that end face; this graft surface is formed of cancellous bone in the center, and edges of cortical bone on the ends. It is primarily against those edges of cortical bone that the insertion instrument of the present invention pushes in the graft insertion process.

Figure 19:
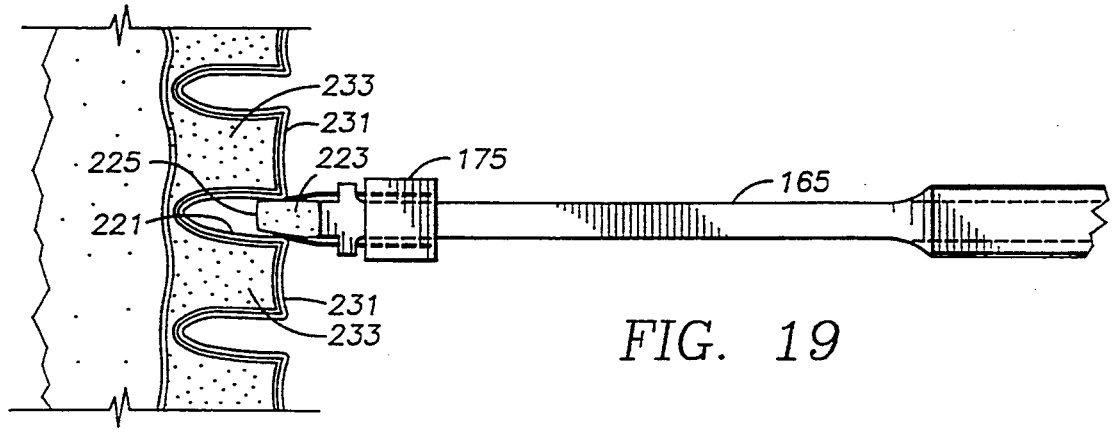

The striking surface 157 of instrument 151 is then tapped lightly, but firmly, with a small mallet or hammer or the like, so that the graft begins to be driven into the disc space 221. This is illustrated in FIG. 19. As the tapping and driving continue, the graft is driven further into the disc space. The fingers 185 do not enter the disc space to any great extent, however, because of their bowed shape, and because they are affixed to the retainer member 175 which is freely slidable along the slide portion 165. Thus, as the graft is driven into the disc space, the terminal end 197 of the abutment head follows the graft into the disc space, but the retainer member 175 remains outside the disc space; it thus slides proximally with respect to the slide portion 165 (or, the slide portion slides distally with respect to the retainer member).

Figure 20:
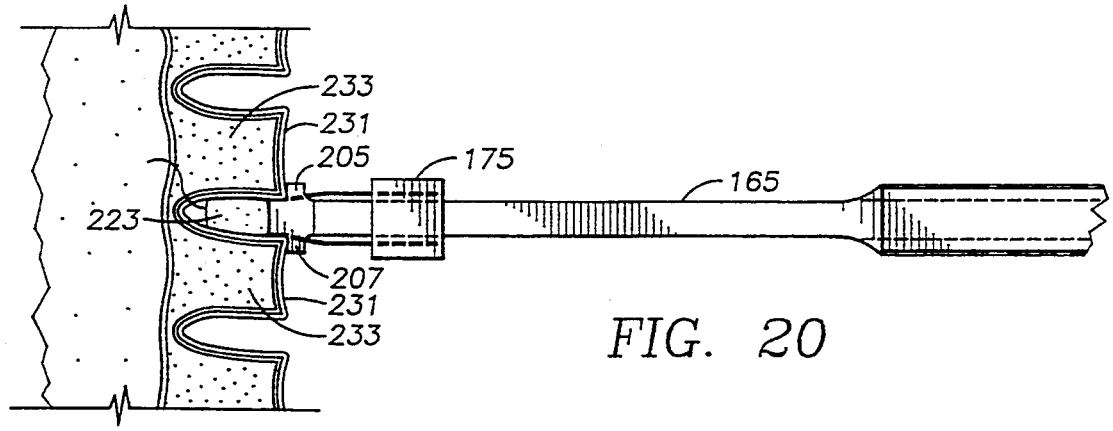
Figure 21:
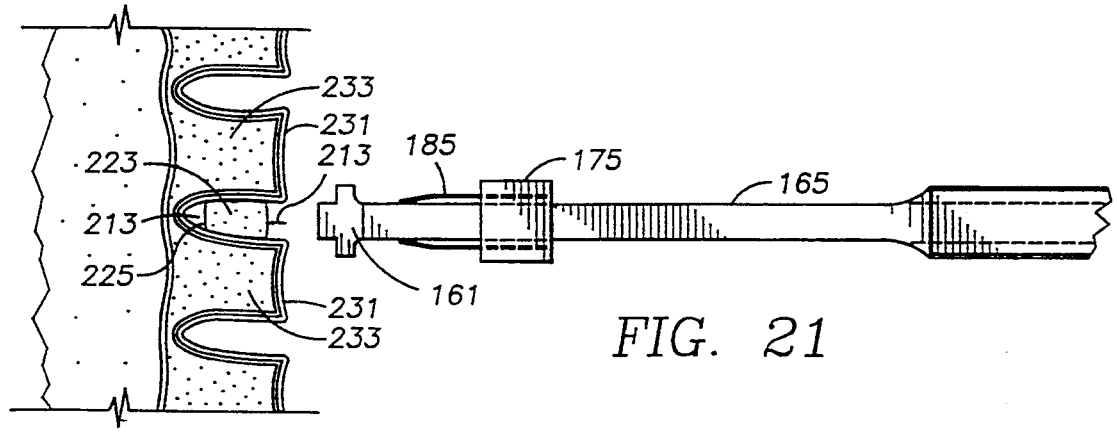

When the stop lugs 205, 207 engage the anterior surfaces 231 of the cervical vertebra 233 bounding the disc space 221, the slide portion 165 cannot move distally any farther, and insertion of the disc is stopped. This is illustrated in FIG. 20. Because of the distance 213 from the lugs 205, 207 to the end face 197 of the abutment head, and hence to the cancellous bone graft surface which it abuts, the graft 223 will be about that same distance 213 from the anterior surfaces 231 of the adjacent vertebra 233 when the instrument is removed, as shown in FIG. 21. Because that distance 213 is only half the depth removed from the grail by using the gauge 137 as discussed above, about the same distance 213 will thus remain at the posterior side of the graft, again as shown in FIG. 21.

It should be appreciated that because of the action of the automatic stop lugs 205, 207 which positively prevents over-insertion of the head of the instrument into the disc space, and because of the centering of the graft which allows for spacing of the graft within the disc space, there is virtually no possibility that a graft will be inserted too far in the space 221, such as would increase the risk of contacting or injuring the spinal cord, pinching the nerves, or causing some other undesired result.

Upon removal of the instrument 151 from the patient's cervical area, it may be cleaned and sterilized for the next procedure.

It should be noted that the instruments described herein are preferably made of stainless steel, or some other surgical quality metal. They are solid and thus relatively heavy, which facilitates their steady handling by the skilled surgeon.

It should also be noted that the instruments described herein, if made the proper size, may be found useful for lumbar interbody fusions, as well as for anterior interbody cervical fusions.

While preferred and alternative embodiments of the invention have been shown and described, many modifications thereof may be made by those skilled in the art without departing from the spirit of the invention.

Therefore, the scope of the invention should be determined in accordance with the following claims.

I claim:

1. An instrument for harvesting an iliac bone graft, comprising:

an elongate handle having a proximal gripping portion terminating in a substantially blunt striking surface, and a distal working portion comprising the distal terminal end of said handle and including a pair of longitudinally extending, transversely spaced apart blade retaining slots, said slots being substantially parallel to the longitudinal axis of said handle and to one another and extending in a proximal direction from said distal terminal end of said handle part way along the length of said handle; and a pair of chisel-type blades adapted for being releasably, lockably housed in said slots said blades each having a main body portion and a shank portion, said shank portions each being adapted for placement in said slots and each having a keyway therein, and wherein said slots each have a longitudinally extending planar base surface and transversely extending, opposed side walls, each of said slots being open in a direction normal to said planar base surfaces at least to the extent of permitting passage of said shank portions into or out of said slots along said normal directions, and said base surfaces each include a transversely extending threaded bore for receiving one of a pair of set screws, said set screws being engageable with said keyways of said blades for locking said blades in said slots.

2. An instrument for harvesting an iliac bone graft, comprising:

an elongate handle having a proximal gripping portion terminating in a substantially blunt striking surface, and a distal working portion including a pair of longitudinally extending, transversely spaced apart blade retaining slots; and a pair of chisel-type blades adapted for being releasably, lockably housed in said slots, wherein said blades each have a main body portion and a shank portion, said shank portions each being adapted for placement in said slots and each having a keyway therein, and wherein said slots each have a longitudinally extending planar base surface and transversely extending, opposed side walls, and said base surfaces each include a transversely extending threaded bore for receiving one of a pair of set screws, said set screws being engageable with said keyways of said blades for locking said blades in said slots, wherein said keyways each have an enlarged portion and a reduced diameter portion disposed distally of said enlarged portion, said enlarged portions being larger in diameter than the largest diameter of said set screws for permitting said blades to be inserted into or removed from said slots through transverse movement of said blades toward or away from said handle, respectively, said set screws being disposed in said reduced diameter portions of said keyways when said set screws are sufficiently loosened, said blades are seated against said base surfaces of said slots, and translated in a proximal direction, said reduced diameter portions being smaller in diameter than the largest diameter of said set screws for preventing transverse movement of said blades with respect to said slots when said set screws are tightened, thereby releasably locking said blades in said slots.

3. An instrument according to claim 2, wherein each of said slots includes a lip disposed on an upper edge of said slots for overhanging a portion of said blades when said blades are fully inserted and releasably locked in said slots.

4. An instrument according to claim 3, wherein said lips extend over the proximal end portions of said slots.

5. An instrument according to claim 4, and further including a transverse bore through said handle disposed proximally of said lips, said transverse bore intersecting said proximal end portions of said slots.

6. An instrument according to claim 3, wherein each of said slots includes a pair of lips disposed on the opposite sides of said slots, such that said lips extend over said shank portions of said blades when said blades are fully inserted and releasably locked in said slots.

7. An instrument according to claim 6, wherein said blades each have recesses disposed on opposite sides of said shank portions for registering with said lips when said enlarged portions of said keyways are in register with said set screws, for permitting transverse movement of said blades into or out of said slots past said lips.

8. An instrument according to claim 1, wherein said blades have working edges on their distal terminal ends which are dual-tapered.

9. An instrument for harvesting an iliac bone graft, comprising:

an elongate handle having a proximal gripping portion terminating in a substantially blunt striking surface, and a distal working portion including a pair of longitudinally extending, transversely spaced apart blade retaining slots; and a pair of chisel-type blades adapted for being releasably, lockably housed in said slots, wherein said blades each have a main body portion and a shank portion, said shank portions each being adapted for placement in said slots and each having a keyway therein, and wherein said slots each have a longitudinally extending planar base surface and transversely extending, opposed side walls, and said base surfaces each include a transversely extending threaded bore for receiving one of a pair of set screws, said set screws being engageable with said keyways of said blades for locking said blades in said slots, wherein said blades have a tapered portion between said shank portion and said main body portion, and said side walls of said slots flare outwardly near the terminal end of said distal working portion for engagement against said tapered portions of said blades when said blades are fully inserted and releasably locked in said slots.

10. An instrument for inserting an iliac bone graft into a disc space, comprising:

an elongate handle having a proximal gripping portion terminating in a substantially blunt striking surface, a distal working portion including an enlarged abutment head on its terminal end, and a slide portion disposed between said proximal gripping portion and said distal working portion, said abutment head having a distal abutment surface for engaging an iliac bone graft; and a bone graft retainer member having a main body slidably disposed on said slide portion of said handle and slidable between said abutment head and said proximal gripping portions, said retainer member including a pair of retaining fingers having proximal ends mounted on said main body of said retainer member and free distal ends, said distal ends of said retaining fingers extending distally beyond said abutment surface of said abutment head when said retaining member is in its distal-most position and including means for gripping a bone graft therebetween, said abutment head including a stop member disposed thereon proximally of, and at a predetermined distance from, said distal abutment face for engaging the anterior surfaces of vertebrae bounding said disc space and limiting the travel of said instrument into said disc space to substantially said predetermined distance.

11. An instrument according to claim 10, wherein said distal ends of said fingers are spring biased toward one another, and spaced apart from one another in an unloaded state a distance less than the height of a bone graft to be gripped.

12. An instrument according to claim 11, wherein said fingers comprise substantially flat spring steel members angled toward one another near their free distal ends.

13. An instrument according to claim 10, said main body of said retainer member having a bore in which said slide portion is received and a track in said bore for closely, slidably receiving a correlatively shaped part of said slide portion for substantially preventing transverse movement, while permitting free sliding movement, of said retainer member with respect to said slide portion.

14. An instrument according to claim 13, wherein said slide portion has a rectangular cross section, and said bore of said retainer member body is also rectangular, said track comprising a pair of grooves disposed in two opposite side walls of said bore for receiving the side walls of said rectangular shaped slide portion therewithin.

15. An instrument according to claim 14, wherein said proximal ends of said retaining fingers are mounted within said bore of said retainer member body, to the two opposite side walls adjacent to said walls having said grooves.

16. An instrument for inserting an iliac bone graft into a disc space, comprising:
an elongate handle having a proximal gripping portion terminating in a substantially blunt striking surface, a distal working portion including an enlarged abutment head on its terminal end, and a slide portion disposed between said proximal gripping portion and said distal working portion, said abutment head having a distal abutment surface for engaging an iliac bone graft; and
a bone graft retainer member having a main body slidably disposed on said slide portion of said handle and slidable between said abutment head and said proximal gripping portions, said retainer member including a pair of retaining fingers having proximal ends mounted on said main body of said retainer member and free distal ends, said distal ends of said retaining fingers extending distally beyond said abutment surface of said abutment head when said retaining member is in its distal-most position and including means for gripping a bone graft therebetween, said slide portion having an upper surface and a lower surface and side surfaces therebetween, said abutment head having upper and lower surfaces substantially coplanar with said upper and lower surfaces of said slide portion and extension portions on each side which extend beyond the side surfaces of said slide portion, said extension portions having a pair of transversely extending stop lugs on their upper surface and a pair of transversely extending stop lugs on their lower surface for engaging the anterior surfaces of vertebrae bounding said disc space and limiting the travel of said instrument into said disc space.

17. An instrument according to claim 16, wherein said stop lugs are spaced proximally from said distal abutment surface of said abutment head a distance substantially equal to a desired offset of the anterior surface of such bone graft from the anterior extremity of such disc space when fully inserted therein.

18. An instrument according to claim 17, wherein said stop lugs on said upper surface and on said lower surface of said extension portions are spaced apart a distance greater than the width of said retaining fingers, said stop lugs, said retaining fingers, and said retainer member being substantially centered with respect to said abutment head and said slide portion such that said retaining fingers may pass freely between said stop lugs during sliding movement of said retainer member along said slide portion.

19. An instrument according to claim 13, wherein said body of said retainer member comprises a pair of substantially C-shaped halves attached together with said slide portion disposed therebetween.

20. A method of inserting an iliac bone graft into a disc space, comprising the steps of:
gripping the bone grail between the distal ends of a retainer member, the retainer member being slidably disposed on a slide portion of the shaft of an insertion instrument;
engaging the central anterior surface of the bone graft with an engagement surface of an abutment head disposed on the distal end of such shaft;
placing the instrument with the gripped bone graft adjacent the anterior extremity of a disc space;
tapping on the proximal end of the shaft to drive it and the bone graft in a distal direction into the disc space, and simultaneously preventing entry of the retainer member into the disc space and sliding the retainer member proximally with respect to the slide portion of the shaft, thereby progressively removing the graft from the retaining fingers as the graft is driven into the disc space.

21. A method according to claim 20, further including the step of limiting the travel of the engagement surface of the abutment head into the disc space.

22. A method of harvesting an iliac bone graft, comprising the steps of:
placing an extraction instrument comprising a proximal blunt striking surface and a distal working portion including a pair of parallel, transversely spaced apart chisel-type blades against the iliac ridge of the ilium of a patient;
tapping the proximal striking surface of the instrument to drive the parallel spaced apart blades into the ilium to a predetermined depth to create a pair of spaced apart parallel incisions in the ilium; and
removing the bone comprised between the parallel incisions from the ilium to form a rough bone graft for subsequent final reshaping.

* * * * *